United States Patent [19]

Krenzer

[11] 4,052,192

[45] * Oct. 4, 1977

[54] 1-(5-t-BUTYL-1,3,4-THIADIAZOL-2-yl)-3-METHYL-5-NONANOYLOXY-1,3-IMIDAZOLIDIN-2-ONE HERBICIDE

[75] Inventor: John Krenzer, Oak Park, Ill.

[73] Assignee: Velsicol Chemical Corporation, Chicago, Ill.

[*] Notice: The portion of the term of this patent subsequent to Oct. 4, 1994, has been disclaimed.

[21] Appl. No.: 668,014

[22] Filed: Mar. 18, 1976

[51] Int. Cl.$^2$ .................... A01N 9/12; C07D 285/12
[52] U.S. Cl. .................... 71/90; 260/306.8 D
[58] Field of Search .................... 71/90; 260/306.8 D

[56] References Cited

U.S. PATENT DOCUMENTS

| 3,758,492 | 9/1973 | Metzger et al. | 71/90 X |
|---|---|---|---|
| 3,759,939 | 9/1973 | Metzger et al. | 71/90 X |
| 3,773,780 | 11/1973 | Metzger et al. | 71/90 X |
| 3,849,432 | 11/1974 | Metzger et al. | 71/90 X |

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

This invention discloses the compound 1-(5-t-butyl-1,3,4-thiadiazol-2-yl)-3-methyl-5-nonanoyloxy-1,3-imidazolidin-2-one and its utility as a herbicide.

3 Claims, No Drawings

1-(5-t-BUTYL-1,3,4-THIADIAZOL-2-yl)-3-METHYL-5-NONANOYLOXY-1,3-IMIDAZOLIDIN-2-ONE HERBICIDE

This invention relates to a new composition of matter and more specifically relates to the new chemical compound 1-(5-t-butyl-1,3,4-thiadiazol-2-yl)-3-methyl-5-nonanoyloxy-1,3-imidazolidin-2-one. This compound has the following structural formula:

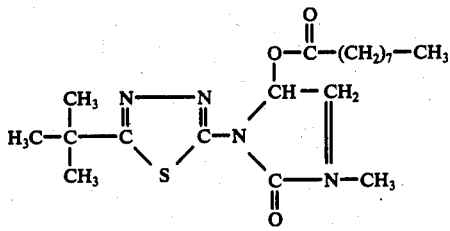

The compound of the present invention is unexpectedly useful as a herbicide.

The preparation of the compound of this invention is shown in the following examples.

EXAMPLE 1

Preparation of 5-t-Butyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel, and the resulting mixture was stirred for a period of about 16 hours, resulting in the formation of a precipitate. The reaction mixture was then purged with nitrogen gas to remove unreacted phosgene. The purged mixture was then filtered to recover the desired product 5-t-butyl-1,3,4-thiadiazol-2-yl isocyanate dimer as a solid having a melting point of 261° to 263° C.

EXAMPLE 2

Preparation of the Dimethyl Acetal of 2-[1-Methyl-3-(5-t-butyl-1,3,4-thiadiazol-2-yl)ureido]-acetaldehyde A mixture of 5-t-butyl-1,3,4-thiadiazol-2-yl isocyanate dimer (6grams), the dimethyl acetal of 2-methylaminoacetaldehyde (3.9 grams) and benzene (50 ml) was charged into a glass reaction flask equipped with a mechanical stirrer and reflux condenser. The reaction mixture was heated at reflux, with stirring for a period of about 5 minutes. After this time the reaction mixture was stripped of benzene to yield an oil which solidified upon standing. The resulting solid was then recrystallized from pentane to yield the desired product the dimethyl acetal of 2-[1-methyl-3-(5-t-butyl-1,3,4-thiadiazol-2-yl)ureido]acetaldehyde having a melting point of 80° to 82° C.

EXAMPLE 3

Preparation of 1-(5-t-Butyl-1,3,4-thiadiazol-2-yl)-3-methyl-5-hydroxyl-1,3-imidazolidin-2-one The dimethyl acetal of 2-[1-methyl-3-(5-t-butyl1,3,4-thiadiazol-2-yl)ureido]acetaldehyde (16 grams), concentrated hydrochloric acid (10 ml) and water (500 ml) were charged into a glass reaction vessel equipped with a mechanical stirrer, thermometer and reflux condenser. The reaction mixture was heated at reflux for a period of about 15 minutes. The reaction mixture was filtered while hot, and the filtrate was then cooled, resulting in the formation of a precipitate. The precipitate was recovered by filtration, dried and was recrystallized from a benzene-hexane mixture to yield the desired product 1-(5-t-butyl-1,3,4-thiadiazol-2-yl)-3-methyl-5-hydroxy-1,3-imidazolidin-2-one having a melting point of 133° to 134° C.

EXAMPLE 4

Preparation of 1-(5-t-Butyl-1,3,4-thiadiazol2-yl)-3-methyl-5-nonanoyloxy-1,3-imidazolidin-2-one 1-(5-t-Butyl-1,3,4-thiadiazol-2-yl)-3-methyl-5-hydroxy-1,3-imidazolidin-2-one (8.0 grams), nonanoyl chloride (5.5 grams) and pyridine (30 ml) were charged into a glass reaction flask equipped with a mechanical stirrer and thermometer. The reaction mixture was stirred for several minutes and was then allowed to stand for a period of about 2 hours. After this time water (100 ml) and hexane (30 ml) were added to the mixture. The organic phase was then separated from the aqueous phase and was washed with water and dilute aqueous sodium bicarbonate. The washed solution was then dried over anhydrous magnesium sulfate and passed through a 3-inch layer of Florex. The filtrate was then stripped of solvent, leaving the desired product 1-(5-t-butyl-1,3,4-thiadiazol-2-yl)-3-methyl-5-nonanoyloxy-1,3-imidazolidin-2-one as an oil.

For practical use as a herbicide the compound of this invention is generally incorporated into herbicidal compositions which comprise an inert carrier and a herbicidally toxic amount of the compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compound is sufficiently soluble in common organic solvents such as kerosene or xylene so that it can be used directly as a solution in these solvents. Frequently, solutions of herbicides can be dispersed under superatmospheric pressure as aerosols. However, preferred liquid herbicidal compositions are emulsifiable concentrates, which comprise the active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 5

Preparation of a Dust

| | |
|---|---|
| Product of Example 4 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compound of this invention can be applied as a herbicide in any manner recognized by the art. One method for the control of weeds comprises contacting the locus of said weeds with a herbicidal composition comprising an inert carrier and as an essential active ingredient, in a quantity which is herbicidally toxic to said weeds, the compound of the present invention. The concentration of the new compound of this invention in the herbicidal compositions will vary greatly with the type of formulation and the purpose for which it is designed, but generally the herbicidal compositions will comprise from about 0.5 to about 95 percent by weight of the active compound of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compound of the present invention is also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compound of the present invention provide herbicidal compositions which are more effective in controlling weeds and often provide results unattainable with separate compositions of the individual herbicides. The other herbicides, defoliants, dessicants and plant growth inhibitors, with which the compound of this invention can be used in the herbicidal compositions to control weeds, can include chlorophenoxy herbicides such as 2,4-D, 2,4,5-T, MCPA, MCPB, alachlor, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro- N,N-dimethylacetamide, CDEA, CDAA, alpha-chloro-N-isopropylacetamide, 2-chloro-N-isopropylacetanilide, 4-(chloroacetyl)-morpholine, 1-(chloroacetyl)piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters foxtail, crabgrass, wild mustard, field pennycress, ryegrass, goose grass, chickweed, wild oats, velvetleaf, purslane, barnyard grass, smartweed, knotweed, cocklebur, wild buckwheat, kochia, medic, corn cockle, ragweed, sowthistle, coffeeweed, croton, cuphea, dodder, fumitory groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compound of this invention is particularly valuable for weed control because it is toxic to many species and groups of weeds while it is relatively nontoxic to many beneficial plants. The exact amount of the compound required will depend on a variety of factors, including the hardiness of the particular weed species, weather, type of soil, method of application, the kind of beneficial plants in the same area, and the like. Thus, while the application of up to only about one or two ounces of the active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compound of this invention can be illustrated by many of the established testing techniques known to the art, such as pre- and post-emergence testing.

The herbicidal activity of the compound of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the test compound formulated as an aqueous emulsion of an acetone solution containing emulsifiers was sprayed at the indicated concentrations on the surface of the soil. After spraying, the soil containers were placed in the greenhouse and provided with supplementary heat as required and daily or more frequent watering. The plants were maintained under these conditions for a period of from 21 to 28 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of the compound is demonstrated by the following data:

TABLE I

| Weed Species | Days After Treatment | Injury Rating (Concentration in lbs/A) | | |
|---|---|---|---|---|
| | | ½ | ¼ | ⅛ |
| Yellow Nutsedge | 21 | 9 | 0 | 0 |
| | 28 | 6 | 0 | 0 |
| Wild Oats | 21 | 9 | 9 | 9 |
| | 28 | 10 | 10 | 10 |
| Jimsonweed | 21 | 9 | 9 | 3 |
| | 28 | 7 | 6 | 3 |
| Velvetleaf | 21 | 10 | 10 | 10 |
| | 28 | 10 | 10 | 10 |
| Pigweed | 21 | 9 | 9 | 8 |

TABLE I-continued

| Weed Species | Days After Treatment | Injury Rating (Concentration in lbs/A) | | |
|---|---|---|---|---|
| | | ½ | ¼ | ⅛ |
| | 28 | 9 | 9 | 7 |
| Wild Mustard | 21 | 10 | 10 | 10 |
| | 28 | 10 | 10 | 10 |
| Yellow Foxtail | 21 | 9 | 6 | 5 |
| | 28 | 7 | 8 | 0 |
| Barnyardgrass | 21 | 9 | 9 | 9 |
| | 28 | 10 | 10 | 7 |
| Crabgrass | 21 | 4 | 5 | 4 |
| | 28 | 5 | 4 | 0 |
| Cheatgrass | 21 | 10 | 10 | 5 |
| | 28 | 10 | 8 | 0 |
| Morningglory | 21 | 10 | 10 | 10 |
| | 28 | 10 | 10 | 10 |

The herbicidal activity of the compound of this invention was also demonstrated by experiments carried out for the post-emergence control of a variety of weeds. In these experiments the compound was formulated as an aqueous emulsion and sprayed at the indicated dosage on the foliage of the weeds that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretofore described. The effectiveness of the compound is demonstrated by the following data:

| Weed Species | Injury rating (Concentration in lbs/acre) | | |
|---|---|---|---|
| | ½ | ¼ | ⅛ |
| Yellow Foxtail | 10 | 10 | 10 |
| Wild Mustard | 10 | 10 | 10 |
| Johnsongrass | 10 | 10 | 4 |
| Pigweed | 10 | 10 | 10 |
| Morningglory | 10 | 10 | 10 |
| Crabgrass | 10 | 10 | 5 |
| Wild Oats | 10 | 10 | 10 |
| Bindweed | 10 | 10 | 10 |
| Jimsonweed | 10 | 10 | 8 |
| Barnyardgrass | 10 | 10 | 10 |
| Yellow Nutsedge | 3 | 4 | 4 |

I claim:
1. The compound 1-(5-t-butyl-1,3,4-thiadiazol-2-yl)-3-methyl-5nonanoyloxy-1,3-imidazolidin-2-one.
2. A herbicidal composition comprising an inert carrier and, as an essential active ingredient, in a quantity toxic to weeds, the compound of claim 1.
3. A method of controlling weeds which comprises contacting the weeds with a herbicidal composition comprising an inert carrier and, as an essential active ingredient, in a quantity toxic to weeds, the compound of claim 1.

* * * * *